(12) United States Patent
Kussick

(10) Patent No.: US 6,461,157 B1
(45) Date of Patent: Oct. 8, 2002

(54) METHOD AND APPARATUS FOR ORTHODONTIC TREATMENT

(75) Inventor: Leon Kussick, Naples, FL (US)

(73) Assignee: RMO, Inc., Denver, CO (US)

( * ) Notice: Subject to any disclaimer, the term of this patent is extended or adjusted under 35 U.S.C. 154(b) by 0 days.

(21) Appl. No.: 09/844,893

(22) Filed: Apr. 27, 2001

(51) Int. Cl.⁷ ............................................. A61C 7/00
(52) U.S. Cl. ....................................................... 433/5
(58) Field of Search ...................... 435/5, 2, 7; 602/17

(56) References Cited

U.S. PATENT DOCUMENTS

| | | | | |
|---|---|---|---|---|
| 4,600,382 A | * | 7/1986 | Forster | 433/5 |
| 4,872,836 A | * | 10/1989 | Grove | 433/5 |
| 5,511,975 A | * | 4/1996 | Schendell | 433/5 |
| 5,620,320 A | * | 4/1997 | Luse et al. | 433/5 |
| 5,667,380 A | * | 9/1997 | Kooiman | 433/5 |

\* cited by examiner

Primary Examiner—Nicholas D. Lucchesi
Assistant Examiner—Melba Bumgarner
(74) Attorney, Agent, or Firm—Sheridan Ross P.C.

(57) ABSTRACT

A device that applies tension to an orthodontic appliance has a tension supplying member connected between first and second elongated straps. The second elongated strap has a series of marked positions along its length differentiated by color. A first connection member connects a position along the length of the first strap to one element of the orthodontic appliance and a second connection member connects one of the indicated positions along the second elongated strap to another element of the orthodontic appliance. Each indicated position corresponds a tension being applied to the orthodontic appliance that is prescribed for a period of orthodontic adjustment. The second connection member engages the second elongated strap at a sequence of indicated positions during successive orthodontic adjustment periods to rapidly increase the prescribed tension on the orthodontic appliance according to a pre-assigned schedule of the orthodontic adjustments. The use of premarked spaced positions permits adjustments for a comfortable, rapid build up of neck strap tension in small increments between visits to the orthodontic practitioner by a patient or a patient's caregiver.

13 Claims, 2 Drawing Sheets

METHOD AND APPARATUS FOR ORTHODONTIC TREATMENT

FIELD OF THE INVENTION

The invention relates to orthodontic treatment and more particularly to arrangements for applying pressure to an orthodontic arch with posterior neck strap type headgear.

BACKGROUND OF THE INVENTION

For orthodontic treatment, an orthodontic appliance such as a face bow is commonly used to apply forces for tooth or alveolar bone repositioning. A face bow generally has an inner bow mountable to bands attached to selected posterior teeth of a patient and an outer bow connected to the inner bow. The attached outer bow extends around and outside on opposite sides of the patient's cheeks. Ends of the outer bow may be detachably secured to a headgear arrangement such as a posterior neck strap. The headgear has one or more tension supplying members such as a spring type device which are connected to the outer bow ends by strap sections extending around the patient's neck. The force applied to the face bow during orthodontic adjustment by the headgear varies and may be adjusted during treatment by changing settings on the tension supplying member or by rearranging the strap sections connecting the tension supplying member to the outer bow.

According to accepted practice, the tension supplied to the appliance (e.g., a neck or cervical head-gear unit) is adjusted under supervision of an orthodontic practitioner during a sequence of office visits. The amount of force applied to the face bow by the neck head-gear unit is initially set for a prescribed interval by the orthodontic practitioner. The neck strap of the headgear is then modified to successively increase the applied force at intervals determined by the orthodontic practitioner. In order for the orthodontic provider to make the force adjustment, the neck strap may include a structure to allow the ends of the outer bow to be attached at varying positions along the strap.

FIG. 1 shows an arrangement of headgear on a patient having uniformly spaced apertures for tension adjustment according to the prior art as disclosed, for example, in U.S. Pat. No. 5,030,088 to S Rogow on Jul. 9, 1991. Referring to FIG. 1, there is shown a neck strap 100 that includes a neck band section 101, a force producing device 120 on the neck band a position adjustment strap section 105 connected to the force producing device 120, adjustment apertures 115-1, 115-2 and 115-3, . . . 115-n in the strap section 105 and a tie rod 110 that is connected to an inner face bow (not shown). During treatment, the tie rod 110 may be initially secured in the aperture 115-1 to apply a first force. In order to increase the force for tooth or mouth positioning, the tie rod is moved as determined by the orthodontic practitioner through the sequence of apertures 115-1 through 115-n. The selection of an aperture of the sequence in FIG. 1 to connect the face bow is reevaluated by the orthodontic practitioner during periodic visits by the patient usually every three or four weeks. Neck straps of headgear as exemplified in FIG. 1 are made with uniformly spaced apertures to aid the orthodontic practitioner in setting the adjustment positions for the patient. It would be advantageous to provide a headgear structure adapted to provide a comfortable, rapid build up of neck strap tension in small increments between visits to the orthodontic practitioner and to have the patient or the patient's caregiver provide the sequence of comfortable, rapid build-up adjustments without consultation with the orthodontic practitioner.

BRIEF SUMMARY OF THE INVENTION

The invention is directed to orthodontic treatment in which tension is applied to an orthodontic appliance by a tension supplying member. A first adjustment arm is connected to one end of the tension supplying member and a second adjustment arm is connected to the other end of the tension supplying member. A first connecting member connects the first adjustment arm to one mouth connecting element of orthodontic appliance and a second connecting member connects the second adjustment arm to another mouth connecting element of the orthodontic appliance.

According to the invention, the second adjustment arm includes a series of indicated positions along its length to which the one end of the second connecting member is engaged. Each indicated position corresponds to application of a prescribed tension to the orthodontic appliance assigned for use during a selected period of orthodontic treatment. The second connection member engages the second adjustment arm at succeeding indicated positions of the sequence to increase the prescribed tension according to a pre-assigned schedule of orthodontic adjustment.

According to an aspect of the invention, each indicated position includes a mark along the length of the second adjustment arm.

According to another aspect of the invention, the marks are differentiated by color according to the pre-assigned schedule of treatment.

According to yet another aspect of the invention, the second connection member engages an element of the orthodontic appliance and engages the second adjustment arm at one of the indicated positions selected according to the pre-assigned schedule.

According to yet another aspect of the invention, the first connecting member engages the first adjustment arm at a position for providing a first prescribed tension for orthodontic treatment when the second connection member engages the second adjustment arm at the first indicated position furthest from the tension supplying member.

According to yet another aspect of the invention, the spacing between the successive indicated positions is set according to the pre-assigned schedule of orthodontic adjustment.

According to yet another aspect of the invention, the sequence of indicated positions on the second adjustment arm includes a sequence of at least first, second, third, fourth and fifth indicated positions in that order with the first indicating position being furthest from the tension supplying member. The spacing between the first and second indicated positions is greater than the spacing between the second and third indicated positions. The spacing between the second and third indicated positions is greater than the spacing between the third and fourth indicated positions and the spacing between third and fourth indicated positions is greater than the spacing between the fourth and fifth indicated positions.

According to yet another aspect of the invention, at least the first, second, third and fourth indicated positions are differentiated by color.

According to yet another aspect of the invention, the second adjustment arm includes a series of indentations along its length. Each indicated position is set in one of the indentations. The second connecting member is inserted into the indentations for the indicated positions according to the pre-assigned schedule and engages the another element of the orthodontic appliance.

According to still yet another aspect of the invention, the tension supplying member is an elastic unit connected between the first and second adjustment arms. The elastic unit may be a coiled spring.

In an embodiment of the invention, a coiled spring in a plastic tube that supplies tension is connected between first and second elongated strap type adjustment arms. The second elongated strap has a sequence of marked positions along its length. A first connection device is detachably engaged with one outer bow end of a face bow and is slidably clamped at a position along the length of the first elongated strap type adjustment arm. A second connection device is detachably engaged with the other outer bow end of the face bow and is slidably clamped at one of the marked positions along the length of the second elongated strap type adjustment arm. The marked positions on the second elongated strap are spaced apart to provide a prescribed sequence of increased tension during successive periods of orthodontic adjustment according to a pre-assigned schedule.

The first position on the second elongated strap nearest its unattached end may be indicated by a black mark. The second position is spaced a prescribed distance from the first position and may be indicated by a blue mark. The third position is spaced from the second mark by a smaller than first to second mark distance and is indicated by a green mark. The fourth position is spaced from the third mark by a smaller than second to third mark distance and is indicated by a yellow mark. The fifth position is spaced from the fourth mark by a smaller than third to fourth mark distance and is indicated by a red mark. Sixth and succeeding positions are uniformly spaced and are indicated by red marks. The sixth and succeeding positions are equally spaced apart by a distance equal to the distance between the fifth and the sixth marks. The spacing between marked positions are precisely determined according to a prescribed course of orthodontic adjustment. For example, movement from one indentation to the next indentation may increase tension by 25 to 30 grams. During treatment, the patient wears the headgear connected to the orthodontic appliance at least for overnight periods and for a child, two or three hours after school.

At the start of an initial period of adjustment, the second connection device is clamped to the first position (black) in from the outer bow on the second elongated strap and the first connection device is clamped at a position on the first elongated strap so that a first tension for the initial period of orthodontic adjustment (e.g., comfortable tension) is applied to the face bow. At the end of the initial orthodontic adjustment period, the second connection device is moved to the second position (blue) on the second elongated strap to increase the tension on the face bow to that prescribed for the second orthodontic treatment period. In the third orthodontic treatment period, the second connection device is clamped at the third position (green) to supply an increased prescribed tension. For the fourth orthodontic adjustment period, the second connection device is clamped at the fourth position (yellow) to supply an increased prescribed tension. For the succeeding periods of orthodontic treatment, the second connection member is sequentially moved to succeeding positions (red) so that the prescribed tension is incrementally increased a prescribed amount (e.g., 25–30 grams). Between the initial positioning and the last adjustment period of a sequence, the tension adjustment may be performed by the patient or the patient's caregiver according to the pre-assigned schedule under prescribed conditions preset by the orthodontic practitioner.

The invention will be better understood from the following more detailed description taken together with the accompanying drawings and the claims.

DETAILED DESCRIPTION

Figure 2:
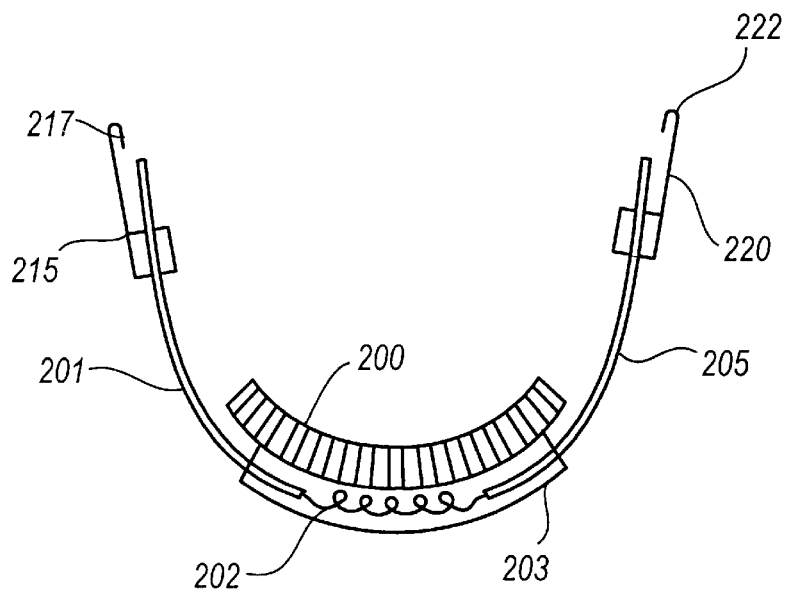
FIG. 2 is a plan view of a device for supplying tension to an orthodontic appliance according to a first embodiment of the invention.

FIG. 2 shows a general view of headgear arrangement on a wearer that applies tension to an outer face bow or other orthodontic appliance in accordance with the invention. In FIG. 2, is shown a neck cushion 200, a left side elongated strap (adjustment arm) 201, coiled spring 202 for supplying tension, a transparent plastic casing 203 for the coiled spring 202, a connection member 215 having an end 217 for connection to an orthodontic appliance (not shown), a right side elongated strap (adjustment arm) 205, and a connection member 220 having an end 222 for connection to the orthodontic appliance (not shown). The left side elongated adjustment arm 201 is fastened to one end of the tension supplying coiled spring 202 in the casing 203. The right side elongated adjustment arm 205 is fastened to the other end of the tension supplying coiled spring 202. The connection member 215 is clamped to a selected position on the left side elongated adjustment arm 201 as will be described and is also connected to the hooked outside arch of a face bow (not shown) by the connection member end 217. The connection member 220 is clamped to one of a sequence of marked positions (not shown) on the right side elongated adjustment arm 205 and is also connected to the hooked outside arch of a face bow (not shown) by the connection member end 222. During orthodontic treatment, the tension provided by the neck strap is increased frequently according to a preassigned schedule by repositioning the connection member 220 along the right side elongated adjustment arm 205 so that the connection member advances toward the coiled spring 202 on the wearer's neck.

Figure 3:
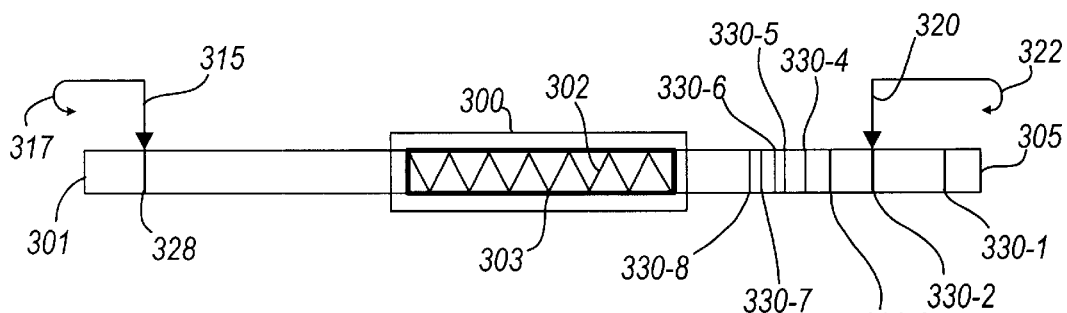
FIG. 3 is a diagrammatic illustration showing the arrangement of a headgear neck strap in the first embodiment of the invention.

FIG. 3 is a diagrammatic representation of a neck strap that may be used in the embodiment of FIG. 2. Referring to the headgear of FIG. 3, there is shown a neck cushion 300, a left side adjustment arm (elongated strap) 301, a tension supplying spring 302, a transparent plastic casing 303, a right side adjustment arm (elongated strap) 305, a left side connecting member 315 having an end 317 that is connected to the outside arch of a face bow (not shown) and right side connecting member 320 having an end 322 connected to the outside arch of the face bow. The connection members may be of the type used in the Precise Spring-Gear™ headgear type J00520 manufactured by RMO Orthodontics, Denver Colorado. Marks 330-1 through 330-7 are positioned along the right side elongated adjustment arm 305 (for a right-handed person) with spacings therebetween varied to provide prescribed increases in tension according to a pre-assigned schedule.

In FIG. 3, the neck cushion 300 is interposed between the neck of the wearer and the tension supplying spring transparent plastic casing 303. One end of each of the elongated adjustment arms 301 and 305 is fastened to an end of the coil spring 302 within the casing 303. The marks 330-1 through 330-8 along the elongated adjustment arm 305 are spaced apart from each other so that the tension applied to the outside arch of a face bow connected to left and right connection ends 317 and 322 may be precisely increased frequently during successive periods of orthodontic treatment according to a pre-assigned schedule by the patient or the patient's caregiver. The marks 330-1 through 330-8 are colored as indicated in table 1 so that the patient or the patient's caregiver may conduct the prescribed routine orthodontic treatment adjustments without consulting the orthodontic practitioner for the sequence of adjustments using the neck strap of FIG. 3. It is to be understood that the number of marks in table 1 is exemplary and more marks may be used for adjustment. Mark 330-1 is positioned nearest the unattached end of the right elongated adjustment arm 305 when the left side connection member 315 is clamped to a position 328 to for a comfortable starting position. The position 328 is not changed during the orthodontic adjustments.

During treatment, the orthodontic appliance such as a two arch face bow and neck strap combination in a cervical headgear which allows a series of frequent adjustments in neck tension increases may be worn by a juvenile patient for two to three hours after school and during night time sleep. In accordance with an exemplary arrangement, the spacing of marks shown in table 1 may be used.

TABLE 1

| PERIOD | MARKED POSITION | SPACING TO NEXT MARK | TIMES OF USE AT MARK | MARK COLOR |
|---|---|---|---|---|
| FIRST INITIAL | 330-1 | COMFORT | 5 | BLACK |
| SECOND | 330-2 | 5 mm | 4 | BLUE |
| THIRD | 330-3 | 4 mm | 3 | GREEN |
| FOURTH | 330-4 | 3 mm | 2 | YELLOW |
| FIFTH | 330-5 | 2 mm | 1 | RED |
| SIXTH | 330-6 | 1.25 mm | 1 | RED |
| SEVENTH | 330-7 | 1.25 mm | 1 | RED |
| CONTINUED | 330-8 etc: | 1.25 mm | 1 | RED |

It is to be understood that Table 1 is only one example and that other mark positions and spacings and use periods may be used.

In the visit to an orthodontic practitioner that initiates the treatment using the frequent adjustment cervical headgear, the connection member 320 of the right side elongated adjustment arm 305 of the neck strap of FIG. 3 is positioned (e.g., clamped) at the mark 330-1 and the connection end 322 is connected to a right outer bow end of a face bow on a right handed patient (e.g., a child). The connection end 317 is connected to the other side of the outer bow of the face bow and the connection member 315 is set at a position along the elongated adjustment arm 301 to supply an initial comfortable starting tension. The initial tension is adjusted by sliding the connection member 315 along the elongated strap 301. The position of the connection member 315 is initially selected by sliding the connection member along the elongated adjustment arm 301 to a position (e.g., 328) at which the neck strap feels comfortable to the patient. The connection member 315 remains at its initially selected position 328 during the entire course of orthodontic treatment and the connection member 320 is moved according to the schedule of table 1 by the patient's caregiver (e.g. parent) to provide frequent incremental increases of prescribed tension according to the pre-assigned schedule.

During the first period of treatment according to table 1, the connection member 320 remains at the black mark 330-1. After a period of five days during which the orthodontic appliance is worn for the prescribed number of hours (e.g., sleep time and two or three after school hours), the connection member 320 is clamped at the blue mark 330-2 along the elongated strap 305 for a period of four days with wear for the prescribed number of hours per day to provide increased tension. The connection member is moved to successive positions along the elongated strap 305 according to the schedule of table 1. Accordingly, the connection member 320 engages the green mark 330-3 during the third period of treatment. During the fourth period of treatment, the connection member 320 engages the yellow mark 330-4. During the fifth period of treatment, the connection member 320 engages the red mark 330-5. In the sixth and subsequent periods of treatment, the connection member 320 engages successive ones of the red marks 330-6, 330-7 etc. along the elongated strap 305. The position adjustments are continued with equal increments in the seventh period and continued periods until the neck pressure is uncomfortably heavy (i.e., wakes the patient from sleep) or if the inner front face bow arch hits upper front teeth too firmly causing soreness of these teeth after a night's wear. If a patient feels soreness upon awakening in the morning, the caregiver stops further adjustments and loosens the neck strap for continued wear.

Advantageously, the sequence of precisely positioned color marks permits the patient's caregiver (e.g. a child's parent) to adjust of the tension provided by the neck strap to an orthodontic appliance such as a prefabricated (properly sized) face bow precisely according to a pre-assigned schedule of adjustment that is physiologically comfortable. The use of the well cushioned headgear arrangement of FIG. 3 permits the orthodontic appliance to be supplied with a precise schedule of prescribed tensions between consultations with the orthodontic practitioner except at the start of treatment, at the termination of the last period in table 1 or upon occurrence of prescribed conditions during the scheduled adjustments. Further, the marks for successive adjustment are located precisely at positions for application of the tension prescribed by the orthodontic practitioner. During the treatment, the caregiver monitors feedback of the patient's comfort and ability to sleep through the night wearing the headgear to assure safety of the treatment.

Figure 4:
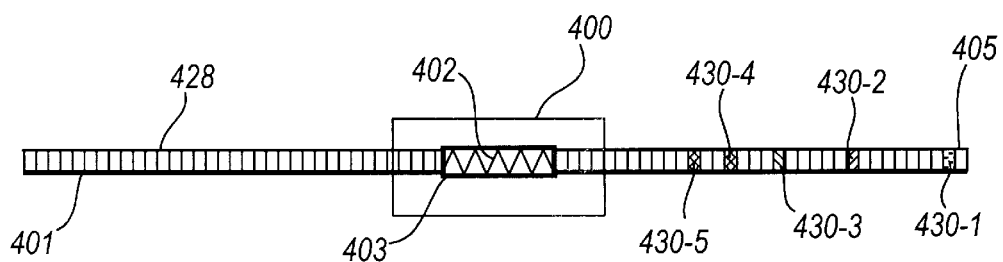
FIG. 4 shows a layout view of an outer surface of a headgear neck strap arrangement according to a second embodiment of the invention.
Figure 5:
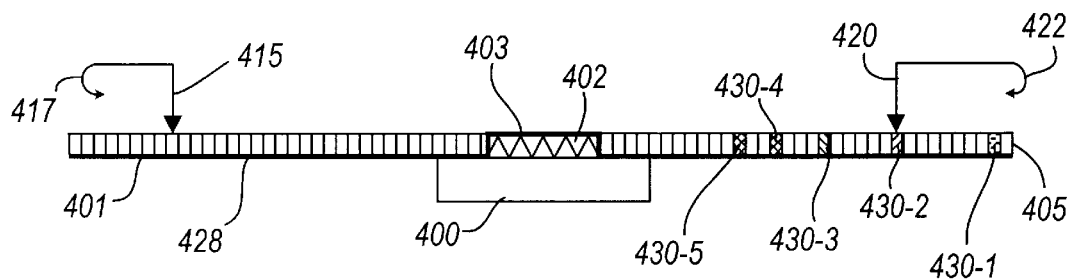
FIG. 5 is a cross-section view of the headgear neck strap arrangement of FIG. 4.

FIGS. 4 and 5 are diagrammatic views of another embodiment of a neck strap for application of tension to an orthodontic appliance according to the invention. The arrangement of FIGS. 4 and 5, utilizes elongated strap type adjustment arms embossed with concatenated rectangular slots which provide regular 2 or 3 millimeter center to center spaced indentations. These rectangular slots permit a clamping engagement by an orthodontic appliance connection member at selected color marked positions along one of the adjustment arms of the headgear neck strap. The selected color markings are on the right side adjustment arm for a right handed person and are along the left side adjustment arm for a left handed person. Referring to FIG. 4, there is diagrammatically shown a neck band cushion 400, a tension supplying coiled spring 402, a transparent plastic casing 403 for the coiled spring 402, an elongated adjustment arm 401 having rectangular slot shaped indentations therealong, an elongated adjustment arm 405 having rectangular slot shaped indentiations therealong including marked rectangular indentations 430-1 through 430-5. The elongated neck straps may be of the type used in the Precise Spring-Gear™ headgear type J00520 manufactured by RMO Orthodontics, Denver Colo.

FIG. 5 is a diagrammatic view of a longitudinal cross-section of the neck strap of FIG. 4 and also illustrates a connection member 415 with a connection end 417 and a connection member 420 having a connection end 422. The connection member ends 417 and 422 are detachably engagable (e.g., by hooks) with the outer bow structure (e.g., hooks) of a face bow or with elements of another type of orthodontic appliance. The connection members 415 and 420 may be of the type used in the Precise Spring-Gear™ head gear type J00520 manufactured by RMO Orthodontics, Denver Colo.

Figure 1:
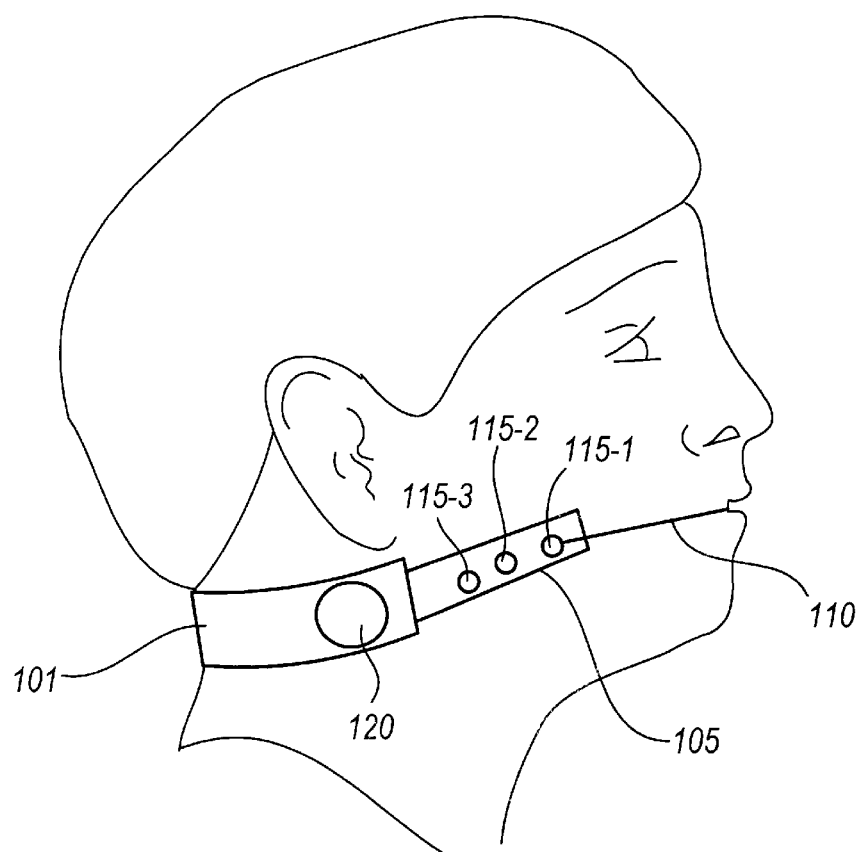
FIG. 1 depicts a view of a device for supplying tension to an orthodontic appliance according to the prior art.

In use, the neck strap of FIGS. 4 and 5 is set in place around the neck of a wearer as shown in FIG. 1 so that the coiled spring 402 in the casing 403 are isolated from the wearer's neck by the neck band cushion 400. The neck band cushion may be made of a foam material that provides a cushion for the wearer's comfort. Selected rectangular slots 430-1 through 430-5 at positions for applying prescribed tensions to an orthodontic appliance during successive periods of orthodontic treatment identified by a varying color arrangement. The outermost rectangular slot 430-1 may be black in color. The sequence of rectangular slots 430-2, 430-3, 430-4 and 430-5 may be blue, green, yellow, red, ... red in color.

As an initial step in orthodontic treatment with the neck strap of FIGS. 4 and 5, the connection member 420 is engaged with the outermost marked rectangular slot 430-1 along the elongated adjustment arm 405 and is also engaged with one end of an orthodontic appliance (e.g., the outer arch of a face bow) when the appliance (e.g., inner arch of the face bow) is placed in the mouth of a wearer. The connection member 415 is engaged the other end of the orthodontic appliance (e.g., other outer arch) and with a rectangular slot along the elongated strap 401 selected to provide a first prescribed (comfortable) tension for the wearer (e.g., 428). The neck strap is worn for a first number of after school hours and sleep time periods using the rectangular slot position 428 on elongated strap 401 and rectangular slot position 430-1 on elongated strap 405. The connection member 420 is then moved to engage the blue marked position 430-2 by the wearer or the wearer's caregiver, and the neck strap is worn for a second number of after school and sleep time periods with the connection members 415 and 420 at rectangular slot positions 428 and 430-2. In the succeeding periods of the orthodontic treatment, the connection member 420 is successively repositioned to be at each of rectangular slots 430-3, 430-4 and 430-5 for a prescribed number of hours after school plus sleep time periods. The movement of the connection member 420 among the marked positions of the right side elongated adjustment arm 405 may follow a prescribed schedule such as shown in table 2.

TABLE 2

| PERIOD | MARKED POSITION | SPACING TO NEXT MARK | DAYS OF USE AT MARK | MARK COLOR |
|---|---|---|---|---|
| FIRST-INITIAL | 430-1 | comfort | 8 | BLACK |
| SECOND | 430-2 | 8 mm | 8 | BLUE |
| THIRD | 430-3 | 6 mm | 6 | GREEN |
| FOURTH | 430-4 | 4 mm | 5 | YELLOW |
| FIFTH | 430-5 | 2 mm | 2 | RED |
| CONTINUED | NOT SHOWN | 2 mm | 2 | NOT SHOWN |

The adjustments may be continued according to the fifth period specification until the neck pressure is to heavy (i.e., wakes the patient from sleep) or if the front face bow arch hits upper front teeth too firmly after a night's wear. The state of the orthodontic treatment is then reevaluated by the orthodontic treatment provider and any further course of treatment if needed with the cervical headgear or otherwise is prescribed. In the event of further treatment using a neck strap of the type shown in FIGS. 4 and 5, the neck strap for further treatment may have another arrangement of marked positions for a different pre-assigned schedule of applied tension. The course of treatment using the neck strap of FIGS. 4 and 5 permits the patient or patient's caregiver to precisely adjust the tension of the neck strap according to the pre-assigned schedule without visiting the orthodontic treatment provider during the course of treatment.

The neck straps of FIG. 3 and FIGS. 4 and 5 may be used as a rapid adjustment cervical head gear for patients generally from 5 to 10 years of age or older to routinely lengthen, expand and retract the maxillary protrusion or overjet and the entire maxillary alveolar arch and teeth mostly in Class II Division I malocclusions. The headgear according to the invention provides rapidly increased tension on the transeptal fibers which connect the maxillary arches, bone and teeth by stretching and pulling both alveolar bone and all attached teeth posteriorly or distally as they allow expansion of the upper arch width and its length and create valuable spaces between the teeth in the entire maxillary arch. The maxillary arch may be expanded to up to 10 mm in the six year molar area and up to 5 mm in the deciduous cuspid area as the six year molars are moved distally within the normal trough that widens. This early expansion of the maxillary arch with its preadolescent bone is stably performed without moving or tipping the posterior teeth buccally using the rapid adjusted cervical head gear eliminates the need for the commonly used of rapid palatal splitting and for expansion or all other types of palatal expansion appliances and also functions to correct overjets (i.e., maxillary alveolar protrusions) while also rotating and aligning anterior teeth and closing routine anterior open bites with overjets.

While the invention has been described by way of particular illustrative embodiments, it is to be understood that the invention is not limited to the above-described embodiments but that various changes and modifications may be made by those of ordinary skill in the art without departing from the scope and spirit of the invention. Accordingly, the foregoing embodiments should not be construed as limiting the scope of the invention which is encompassed instead by the following claims.

What is claimed is:

1. A device for applying tension to an orthodontic appliance, comprising:
   a tension supplying member;
   a first adjustment arm with an end connected to an end of the tension supplying member;
   a first connecting member for connecting another end of the first adjustment arm to one element of the orthodontic appliance;
   a second adjustment arm with an end connected to another end of the tension supplying member and including a sequence of spaced indicated positions; and
   a second connecting member for detachably connecting a selected one of the sequence of indicated positions of the second adjustment arm to another element of the orthodontic appliance,
   wherein each indicated position corresponds to application of a prescribed tension to the orthodontic appliance preset for a period of orthodontic adjustment, and the second connecting member engages the second adjustment arm at successive indicated positions of the sequence during successive periods of the orthodontic adjustment to increase the prescribed tension according to a pre-assigned schedule and wherein the sequence of indicated positions on the second adjustment arm includes a first indicated position furthest from the tension supplying end, and at least a second, a third, a fourth and a fifth indicated position extending toward the tension supplying member in that order, the spacing between the first and second indicated positions being greater than the spacing between the second and third indicated positions and the spacing between the second and third indicated positions being greater than the spacing between the third and fourth indicated positions and the spacing between third and fourth indicated positions being greater than the spacing between the fourth and fifth indicated positions.

2. A device for applying tension to an orthodontic appliance according to claim 1, wherein at least the first, second, third and fourth indicated positions are differentiated by color.

3. A method for applying tension to an orthodontic appliance using a head gear having a tension supplying member, first and second adjustment arms connected to the ends of the tension supplying member, the second adjustment arm including a sequence of spaced indicated positions therealong, a first connection member that connects another end of the first adjustment arm to an element of the orthodontic appliance and a second connection member that connects another element of the orthodontic appliance to the second adjustment arm at a selected one of the indicated positions, the method comprising the steps of:

setting each of the spaced indicated positions to correspond to application of a prescribed tension to the orthodontic appliance for a period of orthodontic adjustment; and engaging the second connection member at successive indicated positions of the sequence during successive periods of orthodontic adjustment to increase the prescribed tension according to a pre-assigned schedule.

4. The method according to claim 3, wherein each indicated position is a marked position along a length of the second adjustment arm.

5. The method according to claim 4, wherein the marked positions are differentiated by color according to the pre-assigned schedule.

6. The method according to claim 3, wherein the second connection member is detachably engaged with the orthodontic appliance element and is detachably engaged with the second adjustment arm at one of the indicated positions selected during a period of orthodontic adjustment according to the pre-assigned schedule of increasing prescribed tension.

7. The method according to claim 3, wherein the first connection member is engaged at a position along the first adjustment arm that provides a first tension for an initial period of orthodontic adjustment when the second connection member is engaged at an indicated position furthest from the tension supplying member.

8. The method according to claim 3, wherein spacings between the successive indicated positions are set according to the pre-assigned schedule of orthodontic adjustment.

9. The method according to claim 3, wherein the sequence of indicated positions on the second adjustment arm is set at a first indicated position furthest from the tension supplying member and at least at a second, a third, a fourth and a fifth indicated position extending toward the tension supplying member in that order, spacing between the first and second indicated positions being set to be greater than spacing between the second and third indicated positions, spacing between the second and third indicated positions being greater the spacing between the third and fourth indicated positions, and the spacing between the third and fourth indicated positions being greater than the spacing between the fourth and the fifth indicated positions.

10. The method according to claim 9, wherein at least the first, second, third and fourth indicated positions are differentiated by color.

11. The method according to claim 3, wherein the second adjustment arm has a series of indentations along its length and each indicated position is in a selected one of the indentations.

12. The method according to claim 11, wherein the series of indentations along the length of the second adjustment arm is a series of rectangular slotted depressions.

13. The method according to claim 11, wherein the second connection member is inserted into indentations for the indicated positions along the second adjustment arm and is engaged with the another element of the orthodontic appliance.

* * * * *